United States Patent [19]

Ito et al.

[11] Patent Number: 6,075,035
[45] Date of Patent: Jun. 13, 2000

[54] CRYSTAL OF HYDRATE AND PROCESS FOR PREPARATION THEREOF

[75] Inventors: Yasuo Ito; Hideo Kato; Shingo Yasuda; Noriyuki Kado; Nobuhiko Iwasaki; Hiroyuki Nishino; Makoto Takeshita, all of Fukui, Japan

[73] Assignee: Hokuriku Seiyaku Co., Ltd., Fukui, Japan

[21] Appl. No.: 09/011,752

[22] PCT Filed: Aug. 23, 1996

[86] PCT No.: PCT/JP96/02352

§ 371 Date: Feb. 23, 1998

§ 102(e) Date: Feb. 23, 1998

[87] PCT Pub. No.: WO97/09330

PCT Pub. Date: Mar. 13, 1997

[30] Foreign Application Priority Data

Sep. 1, 1995 [JP] Japan .................................. 7-248591

[51] Int. Cl.[7] .................................................. A01N 43/42
[52] U.S. Cl. .............................. 514/290; 514/450; 546/89
[58] Field of Search ............................... 546/89; 514/290, 514/450

[56] References Cited

U.S. PATENT DOCUMENTS 5,334,594  8/1994  Ito et al. .................................. 514/291

FOREIGN PATENT DOCUMENTS

| 6-107664 | 4/1994 | Japan . |
| 6-116273 | 4/1994 | Japan . |
| 6-192263 | 7/1994 | Japan . |

OTHER PUBLICATIONS

Chemical Abstract No. 121:205230p, vol. 121, p. 1161, 1994.

Iwasaki et al., Journal of Medicinal Chemistry, vol. 38, No. 3, pp. 496–507, 1995.

Chemical Abstract No. 121:157634z, vol. 121, p. 1026, 1994.

*Primary Examiner*—Dwayne C. Jones
*Attorney, Agent, or Firm*—Greenblum & Bernstein, P.L.C.

[57] ABSTRACT

Dihydrate crystal of 3-[4-(8-fluoro-5,11-dihydrobenz[b]oxepino[4,3-b]pyridin-11-ylidene)piperidino]propionic acid providing high-intensity diffraction peaks at diffraction angles (2θ) of about 4.2°, 17.0°, and 21.3° in a powder X-ray diffraction profile; a medicament comprising the dihydrate crystal; and a process for preparing the dihydrate crystal which comprises the steps of treating a crystalline substance containing an anhydride crystal of the above compound with hydrous acetone, and subjecting the product to drying treatment and moistening treatment.

20 Claims, 2 Drawing Sheets

CRYSTAL OF HYDRATE AND PROCESS FOR PREPARATION THEREOF

CROSS-REFERENCE TO RELATED APPLICATIONS

This application is a National Stage under 35 U.S.C. 371 of International Application No. PCT/JP96/02352, filed Aug. 23, 1996, and claims priority of Japanese Application No. 7-248591, filed Sep. 1, 1995.

BACKGROUND OF THE INVENTION

1. Field of the Invention

The present invention relates to a novel dihydrate crystal of amphoteric tricyclic compound: 3-[4-(8-fluoro-5,11-dihydrobenz[b]oxepino[4,3-b]pyridin-11-ylidene)piperidino]propionic acid which has antihistaminic activity and antiallergic activity and is useful as an active ingredient of medicaments for therapeutic and/or preventive treatment of bronchial asthma, allergic rhinitis, dermatosis, urticaria and other, and also relates to a process for preparing thereof.

2. Description of Background Information

3-[4-(8-Fluoro-5,11-dihydrobenz[b]oxepino[4,3-b]pyridin-11-ylidene)piperidino]propionic acid represented by the following formula (I), first synthesized by the inventor of the present invention, is disclosed in Example 2 of Japanese Patent Unexamined Publication (KOKAI) No. (Hei) 6-192263/1994. This compound was found to have antihistaminic activity and antiallergic activity, and revealed to be useful as active ingredients of medicaments for therapeutic and/or preventive treatment of bronchial asthma, allergic rhinitis, dermatosis, urticaria and other. In the above publication, an anhydride of the compound is specifically disclosed with its physicochemical properties and is described to have a melting point of 160–161° C.

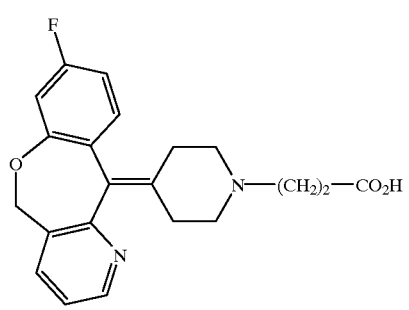

(I)

The inventors of the present invention conducted various researches on processes for recrystallization and purification of a crystalline substance of the compound represented by the aforementioned formula (I), and as a result, they found that the crystalline substances of the compound exist as distinguishable crystalline forms (an anhydride crystal and a dihydrate crystal). The inventors of the present invention recognized that the anhydride of the above compound was susceptible to environmental conditions during storage and not satisfactory from a viewpoint of stability. On the other hand, they revealed that the above dihydrate crystal did not substantially have these problems and had properties highly suitable for active ingredients of medicaments. The existence of the crystalline dihydrate of the compound has not been known so far, and no specific disclosure of the crystal is given in Japanese Patent Unexamined Publication (KOKAI) No. (Hei) 6-192263/1994.

While the inventors of the present invention continued further researches, they were confronted with a problem that, when a crystalline substance of the above compound was isolated and purified in a usual manner, the aforementioned different crystalline forms (anhydride crystal and dihydrate crystal) deposited separately or as a mixture thereof depending on minute fluctuations of manufacturing conditions, and consequently, crystals with constant quality were not obtainable.

When crystalline substances containing a single compound exist as plural forms such as anhydride and hydrate, each of the crystals usually has different physicochemical properties. In particular, when these crystals are used as active ingredients of medicaments, each of the crystalline substances has different characteristics as to absorbability, blood concentration or other, and may often exhibit different bioavailability, which is one of the factors responsible for an effect of a medicament. Therefore, in order to manufacture a medicament which can always achieve constant effect, it is necessary to use a crystalline substance with constant quality as an active ingredient of the medicaments. It is also required to choose a crystalline substance as most suitable form for a medicament from various viewpoints of, for example, effect and stability, and to selectively produce the crystalline substance.

As explained above, the compound represented by the aforementioned formula (I) exist as the aforementioned two crystalline forms, i.e., anhydride and dihydrate, and in addition, a mixture of the two crystalline forms may be produced depending on manufacturing conditions. For these reasons, it is difficult to produce a crystalline substance having constant quality. Therefore, it is desired to develop a method for mass production of the dihydrate of the compound represented by the aforementioned formula (I) in a selective and convenient manner.

SUMMARY OF THE INVENTION

The inventors of the present invention conducted various studies to solve the foregoing problems, and as a result, they found that the dihydrate crystal of the compound represented by the aforementioned formula (I) is stable under a highly humid condition and extremely useful as a medicament. They also found that the dihydrate can be produced selectively and conveniently by a specific method. The present invention was achieved on the basis of the findings.

The present invention thus provides a dihydrate crystal of the compound represented by the aforementioned formula (I). The dihydrate crystal is characterized in that the crystal provides high-intensity diffraction peaks at diffraction angles (2θ) of about 4.2°, 17.0°, and 21.3° in a powder X-ray diffraction analysis. This dihydrate crystal is also characterized in that the crystal provides substantially no high-intensity diffraction peaks at diffraction angles (2θ) of about 11.5°, 19.2° and 22.4° in a powder X-ray diffraction analysis. Furthermore, the dihydrate crystal of the present invention provides a powder X-ray diffraction pattern substantially the same as the X-ray diffraction pattern shown in the attached FIG. 1.

According to another aspect of the present invention, there is provided a process for preparing the aforementioned dihydrate crystal. The process is characterized in that the process comprises the steps of heating a crystalline substance of the compound represented by the aforementioned formula (I) containing anhydride crystals under reflux in a hydrous acetone, and then subjecting the product to drying treatment and moistening treatment.

BEST MODE FOR CARRYING OUT THE INVENTION

Figure 1:
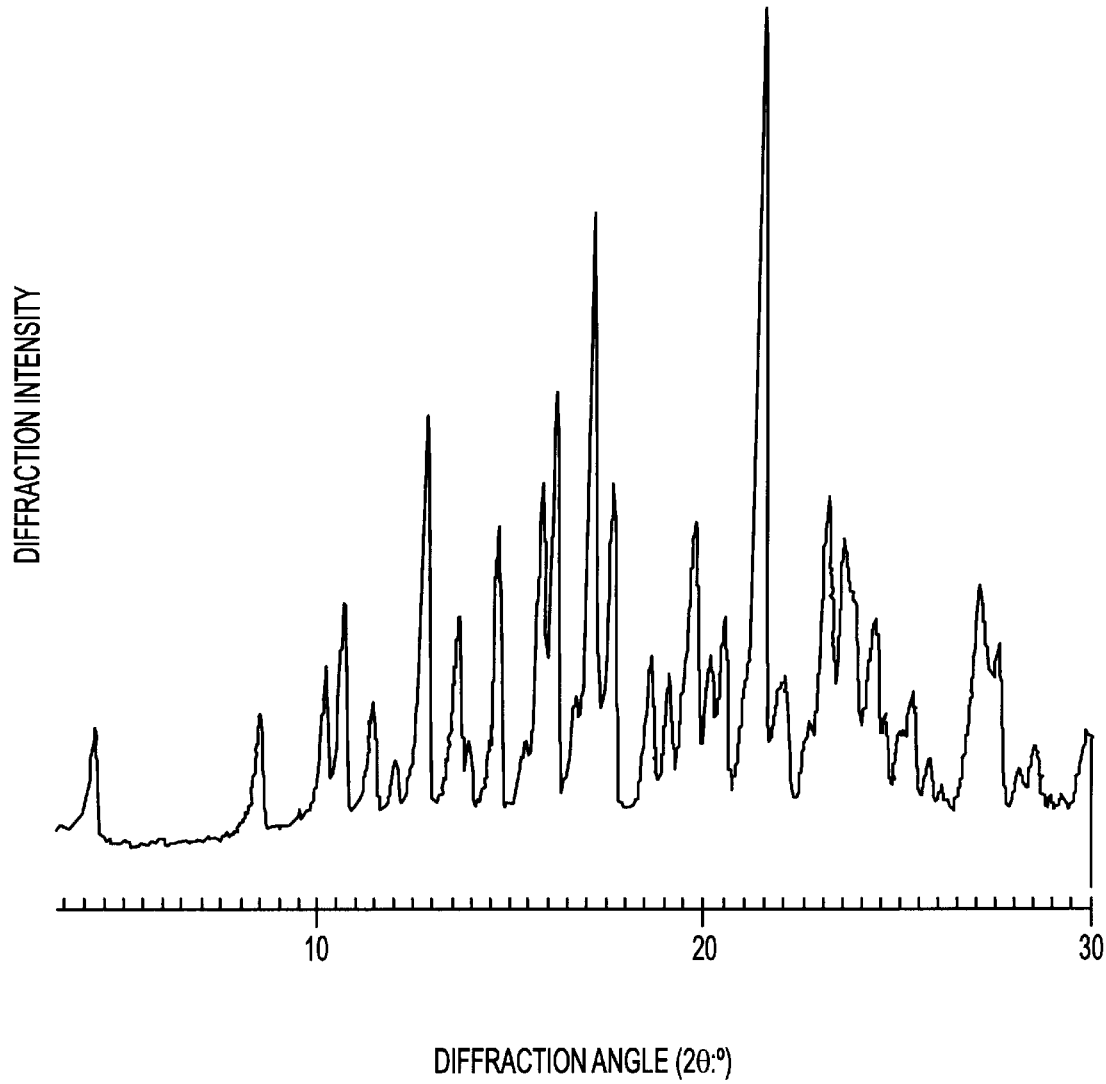
FIG. 1 shows a powder X-ray diffraction pattern of the dihydrate crystal of the present invention.

The dihydrate crystal provided by the present invention is a crystalline substance of the compound represented by the formula (I). The crystal provides a powder X-ray diffraction pattern substantially the same as the powder X-ray diffraction pattern shown in FIG. 1. However, it is known that a powder X-ray diffraction pattern may be obtained with a measurement error depending on measurement conditions. In particular, it is generally known that intensities in a powder X-ray diffraction pattern may fluctuate depending on measurement conditions. Therefore, it should be understood that the dihydrate of the present invention is not limited to the crystal that provides a powder X-ray diffraction pattern completely identical to the powder X-ray diffraction pattern shown in FIG. 1, and that any dihydrate crystals providing a powder X-ray diffraction pattern substantially the same as the aforementioned powder X-ray diffraction pattern fall within the scope of the present invention. Those skilled in the field of powder X-ray diffractometry can readily judge the substantial identity of powder X-ray diffraction patterns.

For example, the dihydrate crystal of the present invention is characterized in that the crystal provides high-intensity diffraction peaks at diffraction angles (2θ) of about 4.2°, 17.0°, and 21.3° in a powder X-ray diffraction analysis. On the other hand, the dihydrate crystal is also characterized in that said crystal provides substantially no high-intensity diffraction peaks at diffraction angles (2θ) of about 11.5°, 19.2°, and 22.4° in a powder X-ray diffraction analysis. Generally, a measurement error of diffraction angle for an usual powder X-ray diffractometry is about 5% or less, and such degree of a measurement error should be taken into account as to the aforementioned diffraction angles. Furthermore, it should be understood that intensities may fluctuate depending on experimental conditions as described above, and accordingly, the order of intensity should not be taken into account as to the three diffraction peaks.

The dihydrate crystal of the present invention can be produced, for example, as explained below. The crystal can be produced by the steps of heating a crystalline substance containing anhydride crystals of the compound represented by the aforementioned formula (I) under reflux in a hydrous acetone, which may optionally be carried out after the crystalline substance is converted into an acetone solvate by the treatment with acetone, and subjecting the product to drying at 50–70° C. and then to moistening treatment under a condition of 40–80% RH (relative humidity). As the crystalline substances, for example, a crystalline substance consisting substantially of anhydride crystals, a crystalline substance consisting of a mixture of the anhydride crystals and the dihydrate crystals of the present invention may be used.

The step of forming acetone solvate, which is optionally employed in the above preparation process, may be performed according to an ordinarily used process. For example, the step may be carried out by adding acetone to the aforementioned crystalline substance and then stirring the mixture, or heating the mixture under reflux for 5 to 30 minutes. As the hydrous acetone used in the subsequent step for the hydrous acetone treatment, an acetone containing 5–10%, preferably about 6–8% of water can be used. The treatment with the hydrous acetone can be performed by suspending the crystalline substance, optionally treated with acetone beforehand, in the hydrous acetone in a ratio of about 20% by weight, and then heating the suspension under reflux for about 5–60 minutes.

The wording "acetone solvate" in the specification means a crystalline substance of the compound represented by the aforementioned formula (I) having incorporated acetone molecules as a crystal solvent. The crystalline substance may have different crystal solvents and/or crystal water incorporated therein. When a crystalline substance of the compound of the aforementioned formula (I) is recrystallized from an organic solvent such as isopropyl alcohol, methanol and then used as a starting material of the process of the present invention, the acetone solvate may preferably be prepared beforehand. Although it is not intended to be bound by any specific theory, a part or whole of a crystal solvent such as isopropyl alcohol incorporated into crystalline lattice as a crystal solvent is replaced with acetone, which facilitates the preparation of the dihydrate in the subsequent steps.

The crystals obtained by the step of the treatment with hydrous acetone is then subjected to drying at 50 to 70° C. for about 10 to 30 hours, followed by allowing the resulting crystals stand at room temperature under a condition of relative humidity of about 40 to 80%, preferably 50 to 70%, for about 1 to 5 hours to produce the dihydrate crystals of the present invention. The anhydride of the compound represented by the aforementioned formula (I) used as a starting material for the preparation of the dihydrate crystal of the present invention can be produced by, for example, the method described in Japanese Patent Unexamined Publication (KOKAI) No. (Hei) 6-192263/1994.

The dihydrate crystal of the present invention, as being a crystalline substance, comprises the compound represented by the formula (I) and is useful as active ingredients of antihistaminic agents and/or antiallergic agents. In particular, the dihydrate crystal of the present invention is characterized in that the crystal has substantially no hygroscopic property under a moistening condition of a relative humidity of 33–84% at 25° C. and is stable after a long-term storage. Accordingly, the crystal is extremely useful for manufacturing the aforementioned medicaments.

Medicaments comprising the dihydrate crystal of the invention are prepared as orally available formulations such as tablets, capsules, powders, fine granules, granules, and syrups, or parenteral formulations such as injections, suppositories, eye drops, and ear drops according to methods ordinarily used for preparing formulations. Medicaments comprising the dihydrate crystal of the present invention as an active ingredient can be used as therapeutic and/or preventive drugs for bronchial asthma, allergic rhinitis, dermatosis, urticaria and other. Dose for a human may be appropriately increased and decreased depending on the symptoms of a patient. Generally, a dose may be 1–500 mg per day for an oral administration to an adult.

EXAMPLES

The present invention will be explained more specifically by referring to the examples. However, the scope of the present invention is not limited to the following examples.

Preparation Example 1

Preparation of 3-[4-(8-fluoro-5,11-dihydrobenz[b]oxepino[4,3-b]pyridin-11-ylidene)piperidino]propionic acid dihydrate (1) Preparation of the compound in free form 3-[4-(8-Fluoro-5,11-dihydrobenz[b]oxepino[4,3-b]pyridin-11-ylidene)piperidino]propionic acid dihydrobromide hydrate (10.9 kg) was dissolved in water (10 liters), and the solution was added dropwise with 10% aqueous sodium hydroxide (9.9 liters) at room temperature to adjust its pH to 6.6. The solution was stirred at −3 to −2° C. for two hours, and the deposited crystals were collected by filtration. The crystals were washed with water (7.5 liters) and dried at 30° C. for 24 hours to obtain pale pink crystals (7.62 kg). Recrystallization from isopropyl alcohol gave pale pink crystals.

(2) Preparation of acetone solvate

Acetone (35 liters) was added to the crystals obtained by the above step (1) (5.04 kg), and the mixture was heated under reflux for ten minutes and then stirred under cooling at 3–8° C. for 2.5 hours. The deposited crystals were collected by filtration to obtain acetone solvate as pale pink crystals (4.29 kg).

(3) Preparation of dihydrate

The crystals obtained by the above step (2) (2 kg) were ground and added with 7% hydrous acetone (10 liters). The mixture was heated under reflux for 30 minutes, and then stirred at 8–10° C. for 30 minutes under cooling. The deposited crystals were collected by filtration, and dried at 60° C. for 17 hours to obtain colorless crystals (1.79 kg). The resulting crystals were allowed to stand under a relative humidity of 50–70% at room temperature for three hours to obtain colorless crystals (1.95 kg) having a melting point of 150–151° C.

NMR spectrum δ (DMSO) ppm: 2.14–2.76 (12H, m), 4.99 (1H, d, J=13 Hz), 5.51 (1H, d, J=13 Hz), 6.60 (1H, dd, J=10.5, 2.5 Hz), 6.70–6.73 (1H, m), 7.06 (1H, dd, J=8.5, 7 Hz), 7.34 (1H, dd, J=7.5, 5 Hz), 7.89 (1H, dd, J=7.5, 1.5 Hz), 8.51 (1H, dd, J=5, 1.5 Hz)

Analysis of water content (Karl Fischer's method)

Calculated: 8.9%, Found: 9.0%

Figure 2:
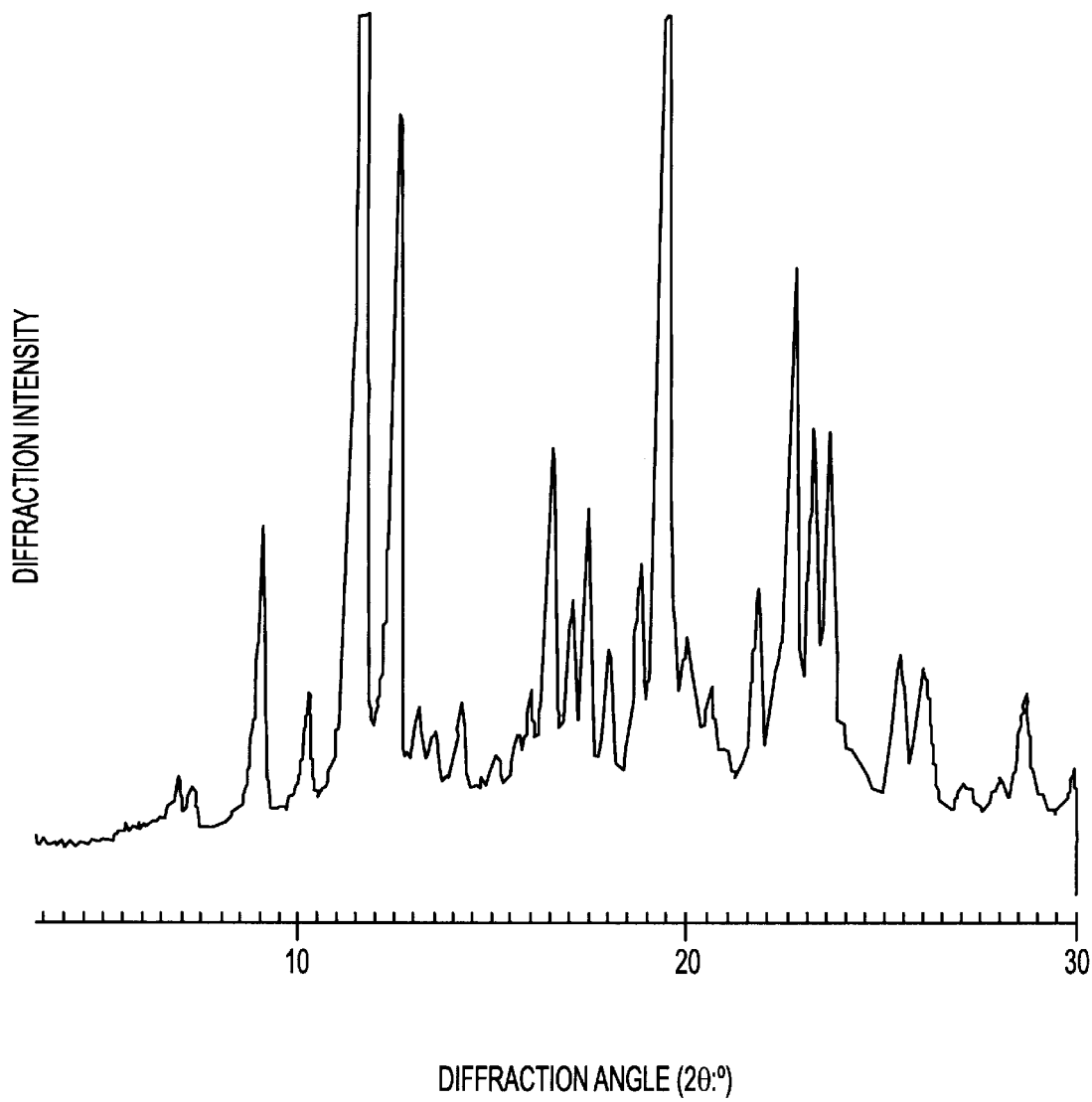
FIG. 2 shows a powder X-ray diffraction pattern of the anhydride crystal disclosed in Japanese Patent Unexamined Publication (KOKAI) No. (Hei) 6-192263/1994.

Powder X-ray diffraction of the dihydrate crystals obtained above and the anhydride crystals disclosed in Japanese Patent Unexamined Publication (KOKAI) No. (Hei) 6-192263/1994 (melting point 160–161° C.) was measured by using Geigerflex Model 2013 diffractometer (Rigaku Denki) (anticathode; Cu, filter: Ni, bulb current: 30 mA, bulb voltage: 30 kV). The powder X-ray diffraction pattern of the dihydrate crystal of the present invention is shown in FIG. 1. The powder X-ray diffraction pattern of the anhydride crystal disclosed in Japanese Patent Unexamined Publication (KOKAI) No. (Hei) 6-192263/1994 is shown in FIG. 2. The dihydrate crystal of the present invention gave high-intensity peaks at diffraction angles (2θ) of about 4.2°, 8.4°, 12.7°, 17.0°, and 21.3°. The anhydride crystal gave no characteristic high-intensity peak at the aforementioned diffraction angles, whereas characteristic high-intensity peaks were observed at diffraction angles (2θ) of about 8.9°, 11.5°, 12.3°, 19.2°, and 22.4°.

Test Example 1

Stability Test (Hygroscopic Test)

The dihydrate crystals of the present invention obtained in Preparation Example 1 and the anhydride crystals disclosed in Japanese Patent Unexamined Publication (KOKAI) No. (Hei) 6-192263/1994 were allowed to stand in a sealed vessel maintained at room temperature (25° C.) and a relative humidity (RH) of 33, 64, 75, or 84% for seven days. Then, a rate of weight alteration was measured as an index of hygroscopic property. The results are shown in Table 1. The anhydride crystals were found to have hygroscopic properties at the humidity conditions other than 33% RH, and hygroscopic rate increased with increasing relative humidity. On the other hand, the dihydrate crystals of the present invention exhibited almost no hygroscopic property under any conditions ranging from 33 to 84% RH.

TABLE 1

| Crystalline substance | Rate of weight alteration (%) | | | |
| --- | --- | --- | --- | --- |
| | 33% RH | 64% RH | 75% RH | 84% RH |
| Dihydrate | −0.09 | −0.05 | 0.24 | 0.35 |
| Anhydride | −0.09 | 2.65 | 7.60 | 13.51 |

Industrial Applicability

The compound of the formula (I) contained in the dihydrate crystal of the present invention is characterized to have excellent antihistaminic activity and antiallergic activity and reduced side effects such as central depression and other. The dihydrate crystal of the present invention has substantially no hygroscopic property and is stable after a long-term storage, and accordingly, the crystal is extremely useful for manufacturing medicaments comprising the aforementioned compound as an active ingredient. Furthermore, according to the process of the present invention, the aforementioned dihydrate crystal can be produced selectively and conveniently, and the process facilitates the preparation of medicaments with constant quality which comprise the aforementioned compound as an active ingredient.

What is claimed is:

1. A 3-[4-(8-fluoro-5,11-dihydrobenz[b]oxepino[4,3-b]pyridin-11-ylidene)piperidino]propionic acid dihydrate crystal.

2. The dihydrate crystal according to claim 1 which provides in a powder X-ray diffraction analysis a powder X-ray diffraction pattern substantially the same as the powder X-ray diffraction pattern shown in FIG. 1.

3. The dihydrate crystal according to claim 2 which provides high-intensity diffraction peaks at diffraction angles (2θ) of about 4.2°, 17.0°, and 21.3° in the powder X-ray diffraction analysis.

4. The dihydrate crystal according to claim 3 which provides substantially no high-intensity diffraction peaks at diffraction angles (2θ) of about 11.5°, 19.2°, and 22.4° in the powder X-ray diffraction analysis.

5. A process for preparing the dihydrate crystal according to claim 3 which comprises treating a crystalline substance containing an anhydride crystal of 3-[4-(8-fluoro-5,11-dihydrobenz[b]oxepino[4,3-b]pyridin-11-ylidene)piperidino]propionic acid characterized with hydrous acetone, and then subjecting the product to drying treatment and moistening treatment.

6. A medicament comprising as an active ingredient the dihydrate crystal according to claim 3.

7. A method for treatment of a condition amenable to a medicament having at least one of antihistaminic activity and antiallergic activity comprising administering a medicament which includes, as an active ingredient, the dihydrate crystal according to claim 3.

8. The dihydrate crystal according to claim 2 which provides substantially no high-intensity diffraction peaks at diffraction angles (2θ) of about 11.5°, 19.2°, and 22.4° in the powder X-ray diffraction analysis.

9. A process for preparing the dihydrate crystal according to claim 2 which comprises treating a crystalline substance containing an anhydride crystal of 3-[4-(8-fluoro-5,11-dihydrobenz[b]oxepino[4,3-b]pyridin-11-ylidene)piperidino]propionic acid characterized with hydrous acetone, and then subjecting the product to drying treatment and moistening treatment.

10. A medicament comprising as an active ingredient the dihydrate crystal according to claim 2.

11. A method for treatment of a condition amenable to a medicament having at least one of antihistaminic activity and antiallergic activity comprising administering a medicament which includes, as an active ingredient, the dihydrate crystal according to claim 2.

12. The dihydrate crystal according to claim 1 which provides high-intensity diffraction peaks at diffraction angles (2θ) of about 4.2°, 17.0°, and 21.3° in the powder X-ray diffraction analysis.

13. The dihydrate crystal according to claim 12 which provides substantially no high-intensity diffraction peaks at diffraction angles (2θ) of about 11.5°, 19.2°, and 22.4° in the powder X-ray diffraction analysis.

14. A process for preparing the dihydrate crystal according to claim 12 which comprises treating a crystalline substance containing an anhydride crystal of 3-[4-(8-fluoro-5,11-dihydrobenz[b]oxepino[4,3-b]pyridin-11-ylidene)piperidino]propionic acid characterized with hydrous acetone, and then subjecting the product to drying treatment and moistening treatment.

15. A medicament comprising as an active ingredient the dihydrate crystal according to claim 12.

16. A method for treatment of a condition amenable to a medicament having at least one of antihistaminic activity and antiallergic activity comprising administering a medicament which includes, as an active ingredient, the dihydrate crystal according to claim 12.

17. The dihydrate crystal according to claim 1 which provides substantially no high-intensity diffraction peaks at diffraction angles (2θ) of about 11.5°, 19.2°, and 22.4° in the powder X-ray diffraction analysis.

18. A process for preparing the dihydrate crystal according to claim 1 which comprises treating a crystalline substance containing an anhydride crystal of 3-[4-(8-fluoro-5,11-dihydrobenz[b]oxepino[4,3-b]pyridin-11-ylidene)piperidino]propionic acid characterized with hydrous acetone, and then subjecting the product to drying treatment and moistening treatment.

19. A medicament comprising as an active ingredient the dihydrate crystal according to claim 1.

20. A method for treatment of a condition amenable to a medicament having at least one of antihistaminic activity and antiallergic activity comprising administering a medicament which includes, as an active ingredient, the dihydrate crystal according to claim 1.

* * * * *